United States Patent [19]

Paoletti et al.

[11] Patent Number: 5,378,457
[45] Date of Patent: Jan. 3, 1995

[54] INTERFERON SENSITIVE RECOMBINANT POXVIRUS VACCINE

[75] Inventors: Enzo Paoletti, Delmar; James Tartaglia, Schenectady, both of N.Y.

[73] Assignee: Virogenetics Corporation, Troy, N.Y.

[21] Appl. No.: 805,567

[22] Filed: Dec. 16, 1991

Related U.S. Application Data

[60] Continuation-in-part of Ser. No. 638,080, Jan. 7, 1991, abandoned, and Ser. No. 537,882, Jun. 14, 1990, Pat. No. 5,110,587, and Ser. No. 537,890, Jun. 14, 1990, Pat. No. 5,174,993, which is a continuation of Ser. No. 234,390, Aug. 23, 1988, abandoned, said Ser. No. 537,882, is a continuation of Ser. No. 90,209, Aug. 27, 1987, abandoned, which is a division of Ser. No. 622,135, Jun. 19, 1984, Pat. No. 4,722,848, which is a continuation-in-part of Ser. No. 446,824, Dec. 19, 1982, Pat. No. 4,603,112, which is a continuation-in-part of Ser. No. 334,456, Dec. 24, 1981, Pat. No. 4,764,330.

[51] Int. Cl.$^6$ ............... A61K 39/275; A61K 39/285; C12N 7/01
[52] U.S. Cl. ............... 424/205.1; 435/235.1; 435/236; 424/232.1; 935/32; 935/65
[58] Field of Search ........... 435/235.1, 236, 172.3, 435/320.1; 424/89, 93 A; 935/32, 57, 65

[56] References Cited

U.S. PATENT DOCUMENTS 5,174,993 12/1992 Paoletti .............................. 424/89

OTHER PUBLICATIONS

Hovanessian, A. G., J. Ifn. Res. 9, 641-647 (1989).
Joklik, W. K., In Interferons in Virology, eds. Fields, B. N., and Knipe, D. M., Raven Press, Ltd., New York, 383-410 (1990).
Paez, E., and Esteban, M., Virology 134, 12-28 (1984).
Rice, A. P. and Kerr, I. M., J. Virol. 50, 209-228 (1984).
Whitaker-Dowling, P., and Youngner, J. S., Virology 131, 128-136 (1983).
Whitaker-Dowling, P., and Youngner, J. S., Virology 152, 50-57 (1986).
Goebel, S. J., Johnson, G. P., Perkus, M. E., Davis, S. W., Winslow, J. P., and Paoletti, E., Virology 179, 247-266, 517-563 (1990).
Ernst, H., Duncan, R. F., and Hershey, J. W. B., J. Biol. Chem. 262, 1206-1212 (1987).
Pathak, V., Schindler, D., and Hershey, J. W. B., Mol. Cell. Biol. 8, 993-995 (1988).
Kaufman, R. M., Davies, M. V., Pathak, V. K., and Hershey, J. W. B., Mol. Cell. Biol. 9, 946-958 (1989).
Davies, M. V., Furtado, M., Hershey, J. W. B., Thimmappaya, B., and Kaufman, R. J., Proc. Natl. Acad. Sci. 86, 9163-9167 (1989).
Dratewka-Kos, E., Kiss, I., Lucas-Lenard, J., Mehta, H. B., Woodley, C. L., and Wahba, A. J., Biochem. 23, 6184-6190 (1984).
Boursnell, M. E. G., Foulds, I. J., Campbell, J. I., and Binns, M. M., J. gen. Virol. 69, 2995-3003 (1988).
Tartaglia, J., Pincus, S., and Paoletti, E., Crit. Rev. Immunol. 10, 13-30 (1990).
Lipman, D. J., and Pearson, W. R., Science 227, 1435-1441 (1985).
Pickup, D. J., Ink, B. S., Hu, W., Ray, C. A., and Joklik, W. K., Proc. Natl. Acad. Sci. 83, 7698-7702 (1986).
Piccini, A., Perkus, M. E., and Paoletti, E., In Meth. Enzymol., eds. Wu, R., and Grossman, L., Academic Press, New York 153, 545-563 (1987).

(List continued on next page.)

*Primary Examiner*—Christine M. Nucker
*Assistant Examiner*—Mary E. Mosher
*Attorney, Agent, or Firm*—Curtis, Morris & Safford

[57] ABSTRACT

What is described is a recombinant poxvirus, such as vaccinia virus, having enhanced sensitivity to interferon. In one embodiment, the recombinant poxvirus has an open reading frame conferring resistance to interferon deleted therefrom. In another embodiment, the recombinant poxvirus is modified to disrupt K3L gene expression. What is also described is a vaccine containing the recombinant poxvirus having enhanced sensitivity to interferon so that the vaccine has an increased level of safety compared to known recombinant poxvirus vaccines.

16 Claims, 6 Drawing Sheets

OTHER PUBLICATIONS

Boyle, D. B., and Coupar, B. E. H., Gene 65, 123–128 (1988).
Falkner, F., and Moss, B., J. Virol. 62, 1849–1854 (1988).
Clewell, D. B., J. Bacteriol. 110, 667–676 (1972).
Clewell, D. B. and Helinski, D. R., Proc. Natl. Acad. Sci. USA 62, 1159–1166 (1969).
Maniatis, T., Fritsch, E. F., and Sambrook, J., Molecular Cloning, Cold Spring Harbor Laboratory, NY 545 pages (1982).
Taylor, J., Weinberg, R., Kawaoka, L., Webster, R. G., and Paoletti, E., Vaccine 6, 504–506 (1988).
Taylor, J., Weinberg, R., Lanquet, B., Desmettre, P., and Paoletti, E., Vaccine 6, 497–504 (1988).
Yuen, L. and Moss, B., Proc. Natl. Acad. Sci. USA 84, 6417–6421 (1987).
Engelke, D. R., Hoener, P. A., and Collins, F. S., Proc. Natl. Acad. Sci. USA 85, 544–548 (1988).
Dreyfuss, G., Adam, S. A., and Choi, Y. D., Mol. Cell. Biol. 4, 415 (1984).
Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
Coccia, E. M., Romeo, G., Nissim, A., Marziali, G., Albertini, R., Affabris, E., Battistini, A., Fiorucci, G., Orsatti, R., Rossi, G. B., and Chebath, J., Virology 179, 228–233 (1990).
Whitaker-Dowling, P., and Youngner, J. S., Virology 137, 171–181 (1984).
Watson, J. C., Hwai-Wen, C., and Jacobs, B. L., Virology 185, 206–216 (1991).
Asch, B. B. and Gifford, G. E., Proc. Soc. Exp. Med. Biol. 135, 419–422 (1970).
Massung, R. F. et al. 1993. Nature vol. 366 pp. 748–751.
Perkus et al. 1991. *Virology* vol. 180 pp. 406–410.
Perkus et al. 1986 *Virology* vol. 152 pp. 285–297.

```
                    10        20         30        40        50
K3L_COP.AA    MLAFCYSLPNAGDVIKGRVYE-KDYALYIYLFDYPHSEA-ILAESVKMHMDRYVE
IF2A$R       MPGLSCRFYQHKFPEVEDVVMVNVRSIAEMGAYVSLLEYNNIEGMILLSELSRRRIRSIN
                10        20        30        40        50        60

60        70        80
K3L_COP.AA    YRDKLVGKTVKVKVIRVDYTKGYIDVNYKRMCRHQ
                  X...   ::::::  .::::::..  X.....
IF2A$R       -KLIRIGRNECVVVIRVDKEKGYIDLSKRRVSPEEAIKCEDKFTKSKTVYSILRHVAEVL
                70        80        90       100       110

IF2A$R       EYTKDEQLESLFQRTAWVFDDKYKRPGYGAYDAFKHAVSDPSILDSLDLNEDEREVLINN
              120       130       140       150       160       170

IF2A$R       INRRLTPQAVKIRADIEVACYGYEGIDAVKEALRAGLNCSTETMPIKINLIAPPRYVMTT
              180       190       200       210       220       230

IF2A$R       TTLERTEGLSVLNQAMAVIKEKIEEKRGVFNVQMEPKVVTDTDETELARQLERLERENAE
              240       250       260       270       280       290

IF2A$R       VDGDDDAEEMEAKAED
              300       310
```

*FIG. 1*

INTERFERON SENSITIVE RECOMBINANT POXVIRUS VACCINE

CROSS REFERENCE TO RELATED APPLICATIONS

This application is a continuation-in-part of copending application Ser. No. 07/638,080 filed Jan. 7, 1991 now abandoned; and a continuation-in-part of copending application Ser. No. 07/537,890 filed Jun. 14, 1990, now U.S. Pat. No. 5,174,993, which in turn is a continuation of application Ser. No. 07/234,390 filed Aug. 23, 1988, now abandoned; and a continuation-in-part of copending application Ser. No. 07/537,882 filed Jun. 14, 1990, now U.S. Pat. No. 5,110,587, which in turn is a continuation of application Ser. No. 07/090,209 filed Aug. 27, 1987, now abandoned, which is a division of application Ser. No. 06/622,135 filed Jun. 19, 1984, now U.S. Pat. No. 4,722,848, which is a continuation-in-part of application Ser. No. 06/446,824 filed Dec. 8, 1982, now U.S. Pat. No. 4,603,112, which is a continuation-in-part of application Ser. No. 06/334,456 filed Dec. 24, 1981, now U.S. Pat. No. 4,769,330, all of which are incorporated herein by reference.

FIELD OF THE INVENTION

The present invention relates to a modified poxvirus and to methods of making and using the same. More in particular, the invention relates to recombinant poxvirus having enhanced sensitivity to interferon.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (17).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (20) and isolated (21,22).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The technology of generating vaccinia virus recombinants has recently been extended to other members of the poxvirus family which have a more restricted host range. The avipoxvirus, fowlpox, has been engineered as a recombinant virus expressing the rabies G gene (23,24). This recombinant virus is also described in PCT Publication No. WO89/03429. On inoculation of the recombinant into a number of non-avian species an immune response to rabies is elicited which in mice, cats and dogs is protective against a lethal rabies challenge.

It is well established that one of the antiviral mechanisms induced by interferon (Ifn) is the inhibition of the initiation of protein synthesis due to the phosphorylation of eIF-2alpha by the P1 kinase (1,2). Vaccinia virus (VV) has been shown to be relatively resistant to Ifn (3,4) and is capable of rescuing Ifn-sensitive viruses from the effects of Ifn (5,6), by somehow reducing the level of eIF-2alpha phosphorylation.

VV-based vaccines are useful immunizing agents (14). Recombinant poxvirus vaccine candidates, particularly VV vaccine candidates, having enhanced sensitivity to interferon, would have an increased level of safety. An Ifn-sensitive phenotype would provide a means for drug intervention in the event that vaccination leads to vaccinial complications.

It can thus be appreciated that provision of a recombinant poxvirus, particularly recombinant vaccinia virus, having enhanced sensitivity to interferon, would be a highly desirable advance over the current state of technology.

OBJECTS OF THE INVENTION

It is therefore an object of this invention to provide recombinant poxviruses, which viruses have enhanced sensitivity to interferon, and to provide a method of making such recombinant poxviruses.

It is an additional object of this invention to provide a recombinant poxvirus vaccine having enhanced sensitivity to interferon and consequently having an increased level of safety compared to known recombinant poxvirus vaccines.

These and other objects and advantages of the present invention will become more readily apparent after consideration of the following.

STATEMENT OF THE INVENTION

In one aspect, the present invention relates to a recombinant poxvirus having an open reading frame conferring resistance to interferon deleted therefrom so that the recombinant poxvirus has enhanced sensitivity to interferon. The poxvirus is advantageously a vaccinia virus.

According to the present invention, the open reading frame deleted from the recombinant poxvirus has homology with eIF-2alpha.

In another aspect, the present invention relates to a recombinant poxvirus modified to disrupt K3L gene expression. The poxvirus is advantageously a vaccinia virus.

In yet another aspect, the present invention relates to a vaccine for inducing an immunological response in a host animal inoculated with the vaccine, said vaccine including a carrier and a recombinant poxvirus having an open reading frame deleted therefrom so that the recombinant poxvirus has enhanced sensitivity to interferon and the vaccine has an increased level of safety compared to known recombinant poxvirus vaccines. The poxvirus used in the vaccine according to the present invention is advantageously a vaccinia virus.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 shows the amino acid sequence (SEQ IN NO: 1) of protein transcribed from the DNA sequence of the K3L open reading frame from the Copenhagen strain of vaccinia virus and the amino acid sequence (SEQ ID NO:2) of protein transcribed from the DNA sequence of eIF-2alpha;

DETAILED DESCRIPTION OF THE INVENTION

Figure 2:
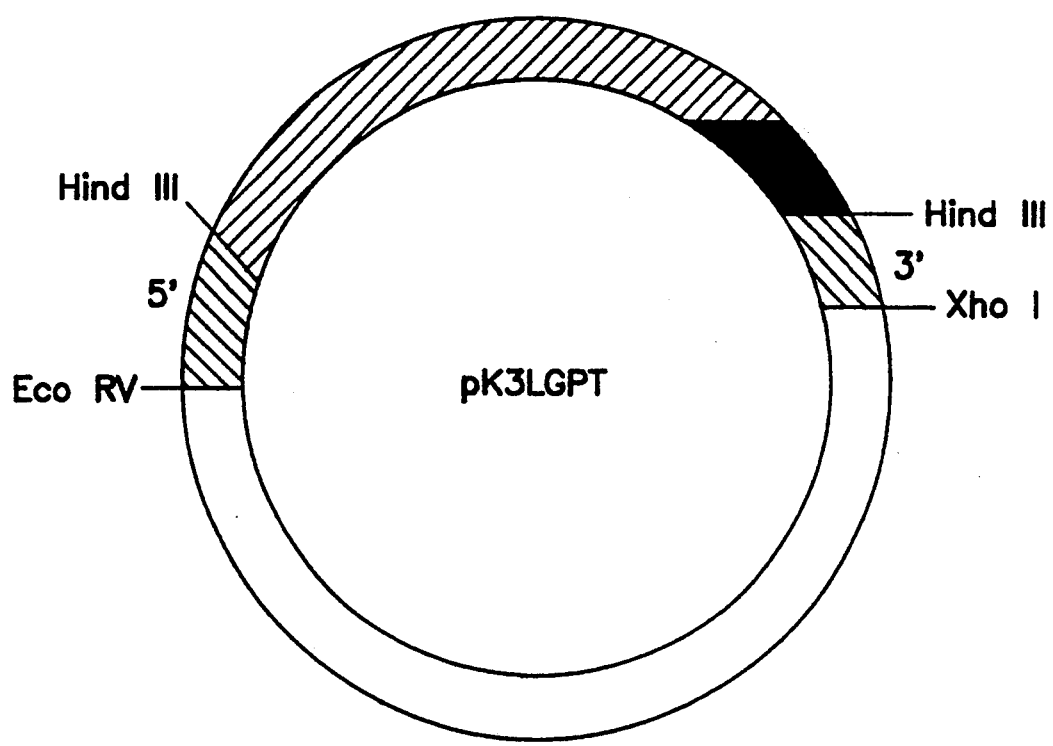
FIG. 2 schematically shows the structure of deletion plasmid pK3Lgpt.

A better understanding of the present invention and of its many advantages will be had from the following examples, given by way of illustration.

EXAMPLE 1

Generation of Vaccina Virus Recombinant vP872 Devoid of the K3L Open Reading Frame Recent elucidation of the complete nucleotide sequence of the VV genome (7) has revealed an open reading frame (ORF), designated as K3L, which has 27.6% identity to eIF-2alpha over an 87 amino acid region. This example describes the generation of a VV mutant, vP872, which was derived by the specific deletion of the K3L ORF from the Copenhagen strain of VV (VC-2).

The amino acid sequence (SEQ ID NO:1) of protein transcribed from K3L ORF identified in VC-2 (7) is presented in FIG. 1 and shown in comparison to the amino acid sequence (SEQ ID NO: 2) of protein transcribed from eIF-2alpha (8). Amino acid homology was obtained using the FASTP (15) program of PCGENE against the Swisprot database release 11.0 (Intelligenetics, Mountain View, Calif.). This alignment has been optimized by gap insertions.

The VV K3L ORF has the potential to encode a 10.5 kDa protein, whereas eIF-2alpha has a calculated molecular mass equal to 36.1 kDa. Furthermore, the 87 amino acid overlap region spans the amino-terminal portion of eIF-2alpha, which contains the serine residue (amino acid 51) which is phosphorylated by the interferon-activated P1 kinase (9). It is the phosphorylation at this residue which is highly correlated with the rapid cessation of protein synthesis in the Ifn-treated system (1,2).

Referring now to FIG. 2, generation of the VV deletion mutant, vP872, was accomplished using the deletion plasmid, pK3Lgpt. Both the upstream (5') and downstream (3') sequences relative to the K3L ORF were derived by PCR. Oligonucleotides K3L5H2 (SEQ ID NO: 3) (5'-ATCATCAAGCTTGT-TAACGGGCTCGTAAAT TGG-3'), K3L52 (SEQ ID NO: 4) (5'-ATCGATATTTTTATGCGT-GATTGG-3'), K3L3H2 (SEQ ID NO: 5) (5'-ATCAT-CAAGCTTTAATTTTTATACCGAAC-3'), and K3L3X2 (SEQ ID NO: 3) (5'-ATCATCCTCGAGG-CAGGCAATAGCGACATAAAC-3') were used for PCR with plasmid, pSD407VC, which contains the VC-2 HindIII K region, as template. Oligonucleotides K3L5H2 (SEQ ID NO: 3) and K3L52 (SEQ ID NO: 3) were used to generate a 227 bp fragment containing 5' sequences with engineered EcoRV and HindIII sites. Oligonucleotides K3L3H2 (SEQ ID NO: 5) and K3L3X2 (SEQ ID NO: 6) were a 239 bp fragment containing 3' sequences with engineered XhoI and HindIII sites. The resultant fragments were digested with the appropriate restriction enzymes and ligated together into pBS-SK (Stratagene, La Jolla, Calif.) vector digested with EcoRV and XhoI. The resultant plasmid was designated pK3LA.

A 1 kb HindIII fragment containing the E. coli gPt gene (ATCC #37145) juxtaposed 3' to a 300 bp fragment derived from the upstream region of the VC-2 hemorrhagic gene (7,16) was inserted into the unique HindIII site of pK3LA, which is situated between the (5') and (3') sequences. The resultant plasmid was designated pK3Lgpt and is depicted schematically in FIG. 2.

This plasmid was used in standard in vitro recombination experiments (17) with wildtype VC-2 as the rescue virus to generate the K3L-minus mutant, vP872. Potential mutants were selected by plating in the presence of medium containing mycophenolic acid as described previously (18,19).

Southern blot analysis of viral DNA derived from the wildtype virus, VC-2, and mutant virus, vP872, confirmed the specific deletion of the K3L gene and demonstrated no further genomic alterations.

EXAMPLE 2

Effect of the K3L Deletion on Protein Synthesis in Ifn-Treated Infected Cells To assess the effect of the K3L deletion on protein synthesis in Ifn-treated infected cells, VC-2 and the deletion mutant, vP872, were inoculated onto L929 cell monolayers (ATCC #CCL1) which had been pretreated with various concentrations of mouse alpha-/beta Ifn. L929 cell monolayers were pretreated for 24 hours with either 0, 10, 100, 500, or 1000 IRU/ml of mouse alpha/beta Ifn (Lee Biomolecular, San Rafael, Calif.). Following pretreatment with Ifn, cell monolayers were mock-infected, or infected with VC-2 or vP872 at an m.o.i. of 100. After a 1 hour adsorption period, the inoculum was removed and 2 ml of methionine-free medium containing 2% dialysed FBS was applied to the monolayers. At 7 hours post infection, the medium was aspirated and 2 ml of the above media supplemented with 25 uCi/ml [$^{35}$S]-methionine (NEN, Boston, Mass.) was applied to the monolayers. At 8 hours postinfection the medium was aspirated from the monolayers and PBS was applied. Lysates were prepared by three cycles of freeze-thawing followed by clarification on the lysate. Total protein concentrations of the lysates were determined using the Bio-Rad Protein Assay kit (Bio-Rad, Richmond, Calif.). Aliquots containing equal quantities of total protein from each sample were fractionated by SDS-PAGE. The gel was fixed by treatment for 45 minutes in a 7.5% acetic acid, 10% methanol, 3% glycerol mixture in deionized water (v/v/v). The gel was prepared for fluorography by washing the gel for 30 minutes in deionized water followed by treatment of the gel for 30 minutes in 1M sodium salicylate. The gel was dried and exposed to film for visualization of the protein species.

As expected, uninfected cell controls showed no effect of Ifn on host protein synthesis even at high concentrations. Results with the wildtype vaccinia virus (VC-2) strain were consistent with previously described results (3,4), in that, viral-induced protein synthesis was resistant to interferon, although a slight diminution was noted at high Ifn concentrations (greater than 500 IRU/ml).

Significantly, it was observed that the deletion of K3L from VC-2 resulted in an enhanced sensitivity of viral-induced protein synthesis to Ifn. Ifn concentrations as low as 10 International Reference Units (IRU)/ml significantly reduced the level of virus-induced protein synthesis in vP872-infected cells. Viral induced protein synthesis in Ifn treated vP872 infected L929 cells was almost completely inhibited at Ifn concentrations of 100 IRU/ml. It is also noteworthy that the enhanced sensitivity to Ifn observed in L929-infected cells cannot merely be attributed to the expression of the E. coli gPt gene. Analysis of a VV (Copenhagen strain) recombinant not devoid of the K3L ORF and containing the identical Ecogpt expression cassette as vP872 displayed an Ifn-resistant phenotype similar to wildtype VV.

Figure 3:
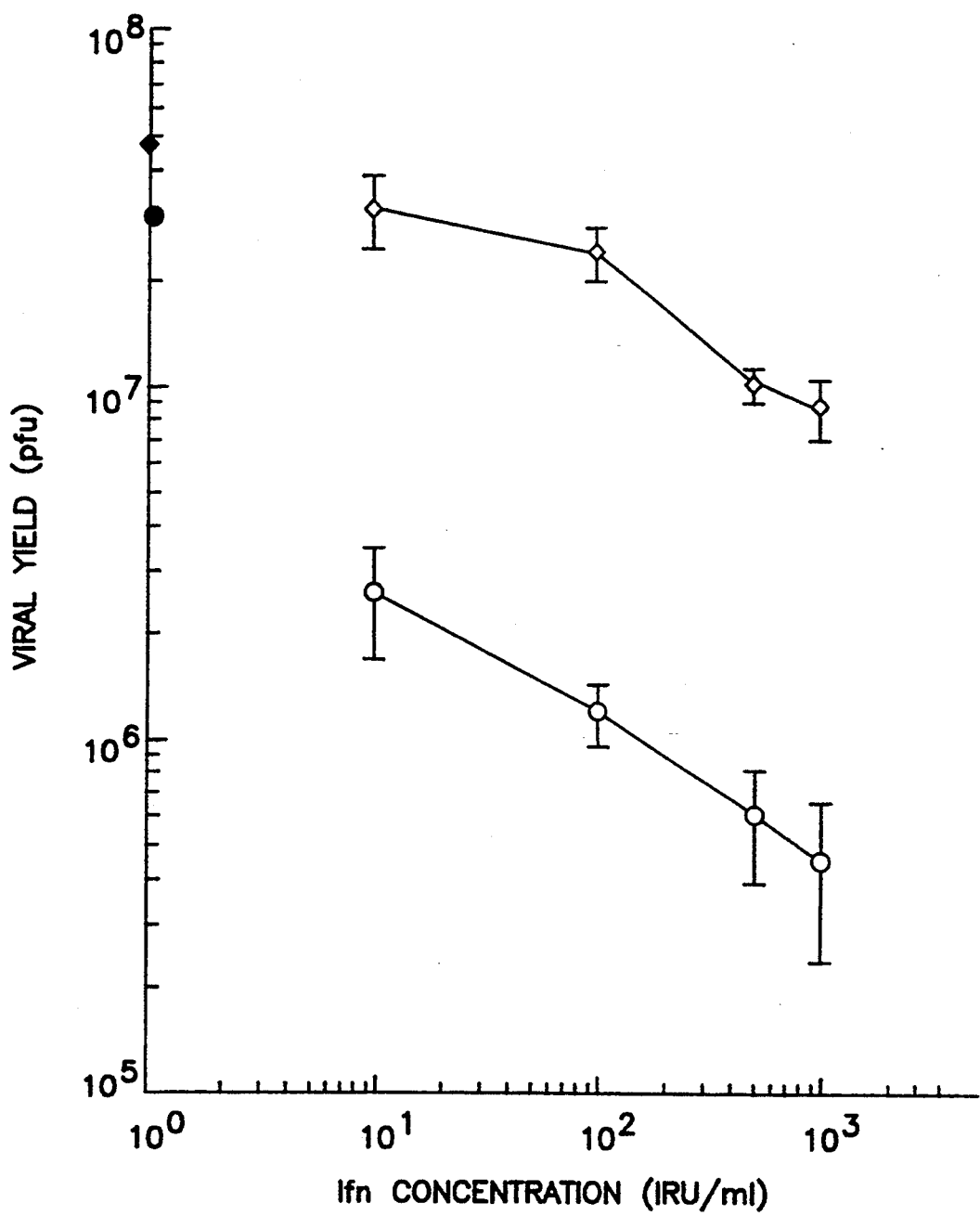
FIG. 3 is a plot of viral yields versus interferon concentration for wildtype and vP872 infected L929 cells.

Similar results demonstrating an increased sensitivity of VV K3L deletion mutants to Ifn were noted in experiments which analyzed the effect of Ifn on virus yields from mutant and wildtype virus-infected L929 cells. The samples were treated identically as described above except that following the adsorption period, 2 ml complete MEM was overlayed, and the samples were harvested at 24 hours post infection (rather than 8 hours) in the liquid overlay. Lysates were prepared as described above without clarification and plated onto monolayers of Veto cells as described previously (17). Samples were inoculated in duplicate and plated in triplicate. Referring now to FIG. 3, viral yields in the absence of interferon are indicated by closed markers on the abscissa. Viral yields as a function of interferon concentration are indicated for wildtype VC-2 infected cells by open diamonds and for vP872 infected cells by open circles. Points represent the average of six plates from a representative experiment. Plates which were harvested immediately following the adsorption period had an average yield of $3.6 \times 10^6$, considered the baseline yield It can be seen that low concentrations of Ifn have a small effect on viral yield in VC-2-infected L929 cells, whereas the same amount of Ifn reduced yield in vP872-infected cells by one log. Concentrations of Ifn greater than 10 IRU/ml reduced viral output in vP872-infected L929 cells to levels below that of input virus. Conversely, in VC-2-infected L929 cells, no concentration of Ifn tested in this experiment was sufficient to reduce viral output below this level.

These results indicate that the VV K3L gene is involved in the Ifn-resistant phenotype described previously for VV (3,4). Previously reported results have demonstrated that (a) an exogenous source of eIF-2alpha could rescue protein synthesis in VSV-infected L cell lysates (10), and (b) an exogenous source of eIF-2alpha was able to overcome the inhibitory effects of eIF-2alpha phosphorylation and enable the replication of a mutant form of adenovirus type 5, which fails to express virus-associated RNA (11,12). Of significance, the plasmid-expressed exogenous source of eIF-2alpha contained an amino acid substitution of a serine to an alanine at position 51, thus preventing the phosphorylation at this position, which is an event highly correlated with translational repression (10). Interestingly, the VV K3L ORF does not contain a serine residue at the equivalent position.

The VV K3L gene plays an integral role in the resistance to interferon by the Copenhagen strain of VV. The WR strain of VV also has a K3L gene (13) which shares homology with eIF-2alpha and differs from its Copenhagen homolog by three base changes, two of which are conservative at the amino acid level. Disruption of K3L gene expression in WR also resulted in an increased sensitivity to interferon.

Thus, recombinant poxvirus containing exogenous DNA coding for an antigen and having disrupted or deleted therefrom an open reading frame conferring resistance to interferon is useful as vaccines because such poxvirus achieves protein synthesis until the levels of interferon are increased as in this example; for instance, until exogenous interferon is administered to the host to "turn off" the recombinant poxvirus. Nonetheless, such recombinant poxvirus will cause the production of sufficient antigen in the host cell, unless increased levels of interferon are present, thereby providing a useful vaccine which can be "turned off" by administration of exogenous interferon. Therefore, with such a recombinant poxvirus vaccine, interferon can be used to treat any post-vaccination complication.

EXAMPLE 3

Reinsertion of K3L ORF Into vP872

To conclusively demonstrate that the increased sensitivity to interferon of the K3L−mutant, vP872, was due to the specific deletion of the K3L ORF, the K3L ORF under the control of its endogenous promoter was reinserted in vP872 at the ATI locus. To accomplish this, an insertion plasmid was engineered as follows: A fragment of 508 bp containing the K3L ORF (7) containing its natural promoter was generated by PCR using oligonucleotides K3L52 (SEQ ID NO: 4) (5'ATCGATATTTTTATGCGTGATTGG-3') and K3LHD (SEQ ID NO: 7) (5'-ATCATCAAGCTTTTATTGATGTCTACACATCC-3') and pSD407 as template (plasmid pSD407 contains the entire HindIII K genomic fragment of vaccinia virus (Copenhagen strain) in the HindIII site of pUCS). This fragment was blunt-ended using the Klenow fragment of the *E. coli* DNA polymerase in the presence of 2mM dNTPs and ligated into pSD541 digested with SmaI and treated with calf intestine alkaline phosphatase. Plasmid pSD541 is a vaccinia insertion plasmid. It is deleted for vaccinia sequences, nucleotide 317,812 through 138,976, encompassing the A25L and A26L ORFs (7). The deletion junction consists of a polylinker region containing XhoI, SmaI and BglII restriction sites, flanked on both sides by stop codons and early vaccinia transcriptional terminators (25). pSD541 was constructed by polymerase chain reaction (PCR) (26) using cloned vaccinia SalI E plasmid pSD414 as template. Synthetic oligonucleotides MPSYN267 (SEQ ID NO: 8) (5' GGGCTCAAGCTTGCGGCCGCTCATTAGACAAGCGAATGAGGGAC 3') and MPSYN268 (SEQ ID NO: 8) (5' AGATCTCCCGGGCTCGAGTAATTAATTAATTTTTATTACACCAGAAAAGACGGCTTGAGATC 3)' were used as primers to generate the left vaccinia arm and synthetic oligonucleotides MPSYN269 (SEQ ID NO: 10) (5' TAATTACTCGAGCCCGGGAGATCTAATTTAATTTAATTTATATAACTCATTTTTTGAATATACT 3') and MPSYN270 (SEQ ID NO: 11) (5' TATCTCGAATTCCCGCGGCTTTAAATGGACGGAACTCTTTTCCCC 3') were used as primers to generate the right vaccinia arm. PCR products consisting of the left and right vaccinia arms were combined, and subjected to PCR amplification. The PCR product was digested with EcoRI and HindIII and electrophoresed on an agarose gel. The 0.8 kb fragment was isolated and ligated into pUC8 cut with EcoRI/HindIII, resulting in plasmid pSD541. Potential transformants containing the K3L ORF were screened for the insert by colony hybridization using a radiolabeled K3L-specific DNA probe. Positives were confirmed by restriction analysis and DNA sequence analysis and designated as pK3LGP.

Plasmid pK3LGP was used in IVR experiments with vP872 as the rescuing virus. Recombinants were screened by hybridization with a radiolabeled K3L-specific probe. Potential recombinant viruses were purified by three rounds of plaque purification. One purified recombinant was amplified and confirmed by DNA restriction analysis of the genomic DNA. The vP872 virus containing the reinserted K3L ORF was designated as vP1046.

To determine the effect of reinserting the K3L ORF under the control of its endogenous promoter on the interferon sensitive phenotype of vP872, the following experiments were performed. Monolayers of mouse L929 cells were pretreated with 0, 10, 100, or 1000 units/ml of mouse $\alpha,\beta$ interferon (Lee Biomolecular, La Jolla, Calif.). These pretreated cell monolayers were either mock infected or infected with VC-2 (wildtype Copenhagen), vP872, or vP1046 at an m.o.i. of 25 pfu/-cell. Virus was adsorbed for one hour at 37° C. with rocking every 10 minutes. At the end of the adsorption period, the inoculum was aspirated and 2 ml of fresh medium was applied to the monolayers. At 7 hour post-infection, the medium was aspirated and 2 ml methionine-free medium containing $^{35}$S-methionine (20 $\mu$Ci/ml) was added. The infected monolayers were pulsed for one hour, the medium was aspirated, washed 1X with PBS, and then harvested by 3 cycles of freeze-thawing in fresh PBS. Total protein content was quantitated using the Bio-Rad Protein Assay Kit (Bio-Rad Laboratories, Richmond, Calif.) and equal protein amounts were fractionated on a 12.5% SDS-polyacrylamide gel (27). The gel was fixed and treated for fluorography with 1% Na-Salicylate.

vP1046 has an interferon-resistant phenotype similar to wildtype VC-2. Virus-specific protein synthesis in vP1046 infected cells was not inhibited to any significant extent except at interferon concentrations of 500 units/ml or greater. In contrast, significant reduction in virus-induced protein synthesis was observed with vP872 at interferon concentrations as low as 10 units/ml.

Viral yields were also analyzed. The experiment was performed in the same way as above except that the infections were harvested at 24 hour post-infection by three cycles of freeze-thawing. Virus progeny was titrated on Vero cells. As observed in the protein analysis above, vP872 replication was severely inhibited by as little as 10 units/ml of interferon (10% the virus yield observed with no interferon), whereas the yields of VC-2 and the K3L restored virus, vP1046, were reduced to these levels at interferon concentrations of 500 units/ml.

EXAMPLE 4

Delection of K3L ORF From the WR Strain of Vaccinia Virus

The WR strain of vaccinia virus has a K3L ORF which is 99% homologous at the amino acid level to the VC-2 K3L ORF (7,13). To determine whether a precise deletion of this K3L ORF from WR has the same phenotypic effect with respect to interferon sensitivity, a deletion plasmid to replace the K3L ORF with the rabies G gene was engineered. PCR-derived fragments of 620 bp and 634 bp, consisting of K3L 5' and 3' flanking arms, respectively, were generated using pSD407 as template. The 620 bp fragment was obtained using oligonucleotides K3LF5 (SEQ ID NO: 12) (CCTTATTTTTATGTTCGGTATAAAAATTAAAGCTTCTTGTTAACGGGCTC- GTAAATTGG) and K3L5X (SEQ ID NO: 13) (AT-CATCTCTAGAGAATTAAGAAGATCCGC). The 634 bp fragment was derived with oligonucleotides K3LF3 (SEQ ID NO: 14) (CCAATTTAC-GAGCCCGTTAACAAGAAGCTTTAATTTT-TATACCGAACATAAAATAAGG) and K3L3RV (SEQ ID NO: 15) (GCGTGTTTTAGTGATAT-CAAACGG). These fragments were then used in equal amounts as template in subsequent PCR fusions using oligonucleotide primers K3L5X (SEQ ID NO: 13) and K3L3RV (SEQ ID NO: 15). This created a fusion between the 5' and 3' sequences with an XbaI site at the 5' end., an intact EcoRV site at the 3' end, and a HindIII site between the arms. The 1.2 kb fragment obtained was blunted using the Klenow fragment of the E. coli DNA polymerase in the presence of 2mM dNTPs and then digested with XbaI. The plasmid vector, pBSgpt, was digested with SmaI and XbaI and the K3L fusion arms were inserted (the plasmid pBSgpt contains the E. coli expression cassette described in generation of vP872). Clones containing the desired insert were screened by colony hybridization using the above PCR product as probe. Clones were confirmed by XbaI/PstI restriction analysis and verified by sequencing. The sequence verified recombinant was designated pK3LAex. This plasmid was partially digested with HindIII and the linear product, consisting of three products differing in the location of HindIII cleavage, was obtained. Plasmid pRW838 was digested with SmaI to liberate a 1.9 kb fragment containing the rabies G gene under control of the H6 promoter. The plasmid pRW838 contains the rabies G gene in an canarypox virus insertion vector. This plasmid was generated in the following manner. Oligonucleotides A through E (A: (SEQ ID NO: 16) CTGAAATTATTTCAT-TATCGCGATATCCGTTAAGTTTGTATC-GTAATGGTTCCTCAGGCTCTCCT GTTTGT; B: (SEQ ID NO: 17) CATTACGATACAAACT-TAACGGATATCGCGATAATGAAATAATTT-CAG; C: (SEQ ID NO: 18) ACCCCTTCTGGTTTTTCCGTTGTGTTTTG-GGAAATTCCCTATTTACACGATC-CCAGACAAGCTTA GATCTCAG; D: (SEQ ID NO: 19) CTGAGATCTAAGCTTGTCTG-GGATCGTGTAAATAGGGAATTTC-CCAAAACA; E: (SEQ ID NO: 20) CAACG-GAAAAACCAGAAGGGGTACAAACAG-GAGAGCCTGAGGAAC) were Kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (28) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter through the entire rabies G gene, was inserted between the NruI and BamHI sites of pRW824. The resulting plasmid was designated pRW832. Insertion into pRW824 added the H6 promoter 5' of NruI. The pRW824 sequence (SEQ ID NO: 21) of BamHI followed by SmaI is: GGATCCCCGGG. pRW824 is a plasmid that contains the infectious bronchitis virus peplomer gene linked precisely to the vaccinia H6 promoter. Digestion with NruI and BamHI completely excises the peplomer gene. The 1.8 kbp pRW832 SmaI fragment, containing the entire H6 promoted rabies G, was inserted into the SmaI site of pRW831. pRW831 is the C5 locus deorfed vector which was derived as follows. The C50RF is contained within pRW764.5. pRW764.5 is a 0.9 kbp PvuII canarypox fragment cloned between the PvuII sites of pUC9. There are two BglII sites in pRW764.5 and they are both in the C50RF. The 320 bp ORF was deleted from the T of C5's translation initiation codon to 30 bp upstream of its stop codon. Replacement of the C5 ORF was achieved by insertion of annealed oligonucleotides RW145 (SEQ ID NO: 22) (5'-ACTCTCAAAAGCTTCCCG-GGAATTCTAGCTAGCTAGTTTTTATAAA-3') and RW146 (SEQ ID NO: 23) (5'-GATCTT-TATAAAAACTAGCTAGCTAGAATTCCCG-GGAAGCTTTTGAGAGT-3') into pRW764.5 which was partially cut with RsaI and fully cut with GltII to delete 306bp. The resulting plasmid, pRW831, contains the following sequence (SEQ ID NO: 24) in place of the C5 ORF: GCTTCCCGGGAATTCTAGCTAGC-TAGTTT. The inserted sequence is followed by TTAT which creates TTTTTAT 3' of rabies G in pRW838.

The 1.9 kbp H6/rabies G fragment was ligated into linearized pK3LAex (described above). Recombinants containing the rabies gene were screened by colony hybridization. Clones that contained the rabies G gene were screened for proper insertion by restriction endonuclease digestion. The recombinant was designated pK3LAR. pK3LAR was used in standard recombination assays with the WR strain of vaccinia virus as the rescuing virus. Screening of this recombinant was by plaque hybridization using a rabies-specific probe. The recombinant generated was confirmed by restriction analysis and designated vP1033.

EXAMPLE 5

The Ability of vP872 to Rescue Vesicular Stomatitis Virus (VSV) and Endomyocarditis Virus (EMC) From the Antiviral Effects of Interferon The ability of vaccinia virus to rescue the interferon sensitive viruses, VSV and EMC, from the antiviral effects of interferon has been well documented (5,6). This is especially interesting since these two viruses are believed to be inhibited by different interferon-induced pathways (5,6,29). This suggests that vaccinia virus can interfere with the interferon-induced antiviral pathways at more than one level. It was of interest to determine whether the vaccinia virus K3L deletion mutant, vP872, had the capacity to rescue these two viruses to the same extent as wildtype virus. To test the rescuing potential of vP872, the following experiment was performed. L929 cells pretreated with 0, 10, 100, or 1000 units/ml of mouse $\alpha/\beta$ IFN were infected with vaccinia (wildtype or the K3L-minus recombinant vP872) at an mol of 1 for 2 hours at 37° C. with rocking every 10 minutes. After 2 hours, the inoculum was aspirated and the monolayers washed with PBS. VSV and EMC were then inoculated onto the monolayers at an moi of 10 in the presence of 5 $\mu$g/ml actinomycin D (Sigma Chemicals, St. Louis, Mo.). After an hour adsorption period at 37° C. (with rocking every 10 minutes), the inoculum was aspirated and 2 ml fresh media added. At 7 hours post infection with VSV or EMC, the media was removed and replaced with methionine-free MEM contaning 20 $\mu$Ci/ml $^{35}$S-methionine. The monolayers were pulsed for 1 hour then harvested by washing twice in PBS and lysing the cells by three cycles of freeze-thawing in 0.5 ml PBS. Total VSV or EMC-specific protein synthesis was evaluated upon fractionation of equal protein quantities by SDS-PAGE (27). Controls consisted of uninfected cells and vaccinia-infected controls not treated with actinomycin D. To determine the effect of vaccinia coinfection on VSV and EMC yields, the infections were performed as above, but they were harvested after 24 hours (without a $^{35}$S-methionine pulse) by three cycles of freeze-thawing. The virus was titered on L929 cells on which vaccinia virus does not plaque but VSV and EMC do form plaques.

Figure 4:
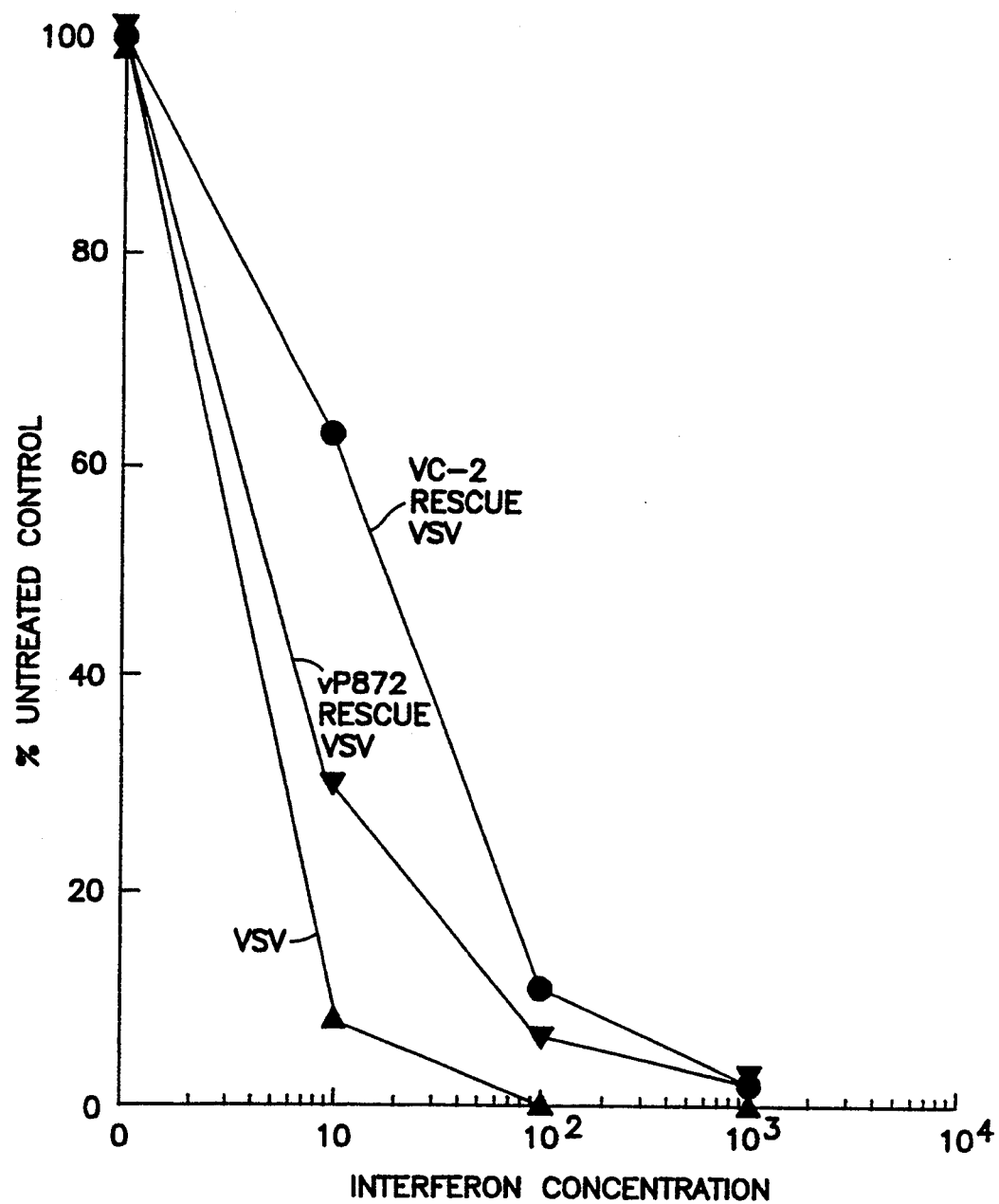
FIG. 4 is a plot of viral yields versus interferon concentration for VSV viruses.
Figure 5:
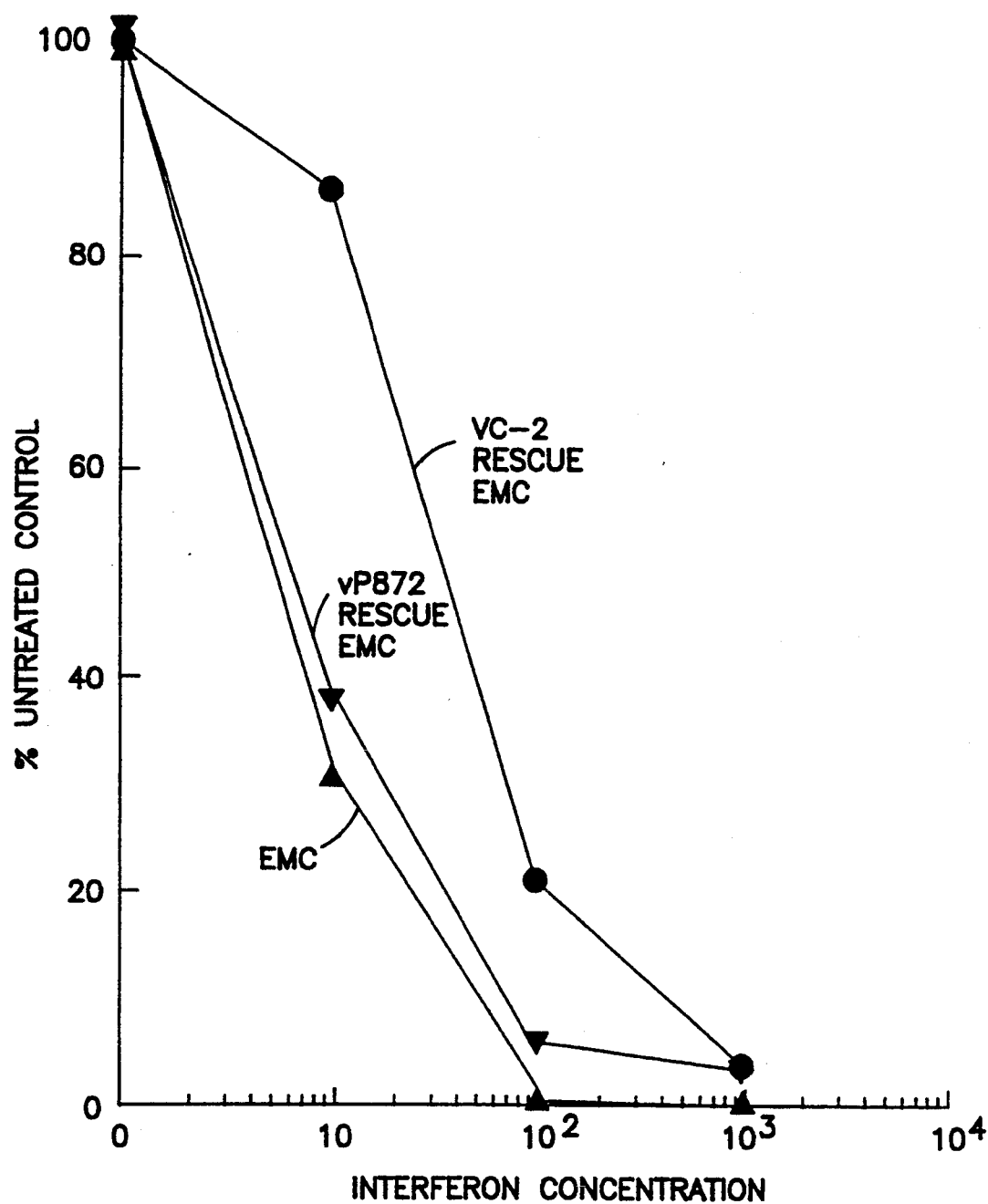
FIG. 5 is a plot of viral yields versus interferon concentration for EMC viruses.

A rescue experiment with VSV and EMC viruses, respectively, at the level of late protein synthesis was performed. VSV-induced protein synthesis was markedly inhibited by interferon concentrations as low as 10 units/ml and was virtually abolished at an interferon concentration of 1000 units/ml. Both VC-2 and vP872 were able to restore VSV-specific protein synthesis at all interferon concentrations tested, although VC-2 was more efficient in this regard. EMC showed moderate interferon sensitivity at concentrations of 10 units/ml and marked sensitivity at interferon concentrations greater that 100 units/ml. Only VC-2 was able to restore protein synthesis to EMC, although it is not as dramatic as the rescue of VSV. These results are shown in FIGS. 4 and 5 for the rescue experiments with VSV and EMC, respectively. It can be seen that VC-2 was able to rescue both VSV and EMC viruses from the antiviral effects of interferon. vP872, on the other hand, was able to rescue only VSV from the antiviral effects of interferon, and even then, not to the same extent as VC-2.

The results for the VSV rescue experiments can be explained from what is known in the literature pertaining to vaccinia virus rescue of this interferon sensitive virus. Interferon is known to inhibit VSV replication in mouse L929 cells largely via translational shutdown (6). This system which shuts down VSV-specific translation is induced by interferon in the presence of double-stranded RNA synthesized during the vital replicative cycle. The presence of these components activates P1 kinase, which itself becomes phosphorylated, and this promotes the phosphorylation of eIF2-α. Phosphorylation of eIF2-α strongly correlates with a cessation of protein synthesis. Vaccinia appears to intercede to block this pathway at two levels. First, vaccinia infection is known to alter the phosphorylation of P1 kinase. Ten times more double-stranded RNA is required to obtain equivalent levels of phosphorylated P1 kinase in lysates from vaccinia infected cells than lysates from uninfected cells (30). This is apparently due to a vaccinia-encoded function designated as SKIF (30) which has characteristics consistent with being the double-stranded RNA binding protein recently identified (31). Second, the K3L gene product apparently affects the downstream portion of this mechanism by acting as a pseudosubstrate of the P1 kinase abrogating its ability to phosphorylate eIF2-α. Therefore, VC-2 which encodes both these functions is much more capable of rescuing VSV from the effects of interferon than vP872. vp872 still retains some capacity to rescue VSV due to its expression of the double-stranded RNA binding protein.

The major antiviral mechanism of interferon upon EMC replication has been shown to be due to RNA breakdown mediated by ribonucleases activated by the interferon-induced 2'-5' adenylsynthetase (29). Since vaccinia virus has the ability to rescue EMC from the effects of interferon, this suggests vaccinia also abrogates this interferon-mediated pathway. In this light, however, why vP872 does not rescue EMC in the presence of interferon is not certain. Perhaps the vaccinia-induced factor that abrogates this antiviral modality is not expressed in sufficient quantities in the K3L-minus virus infected cell to achieve this function.

Nonetheless, this example demonstrates that the recombinant poxvirus of the invention having an open reading frame for interferon resistance disrupted or deleted therefrom can still function with respect to protein synthesis in the presence of interferon, e.g., by expression of the double-stranded binding protein. Thus, a recombinant poxvirus containing exogenous DNA coding for an antigen and having the open reading frame for interferon resistance deleted therefrom is a useful vaccine because it can still function with respect to protein synthesis (thereby allowing sufficient antigen to be produced to stimulate an immune response); and this recombinant poxvirus is even of greater utility because it can be substantially "turned off" when interferon levels are raised, e.g., by administration of exogenous interferon, for instance, in the event of a post-vaccination complication.

EXAMPLE 6

Effect of Infection by vP872 OR vP1033 on Phosphorylation of Host Cell P1 Kinase If the K3L-specified gene product, which is homologous to eIF2-$\alpha$, acts as a pseudosubstrate for the P1 kinase preventing phosphorylation of eIF2-$\alpha$ and the cessation of protein synthesis caused by the phosphorylation of eIF2-$\alpha$, the phosphorylation of P1 kinase would be similar in wildtype (VC-2) and K3L deletion mutant (vP872 and vP1033) infected cells. To investigate the phosphorylation of P1 kinase in these infected cell systems, the following experiment was performed. L929 cells ($5\times10^4$) were plated in a 100mm dish in 10 ml Dulbecco's Modified Eagle Medium (D-MEM; Gibco Laboratories, Grand Island, N.Y.) plus 10% fetal bovine serum (Hyclone Laboratories), 2mM L-glutamine (Gibco Laboratories, Grand Island, N.Y.), and 1% penicillin-streptomycin (Gibco). The medium was aspirated the next day and 2 ml medium containing 0, 10, 100, or 1000 units/ml mouse $\alpha/\beta$ interferon (Lee Biomedical Research, Inc., La Jolla, Calif.) was added. After 24 hours, the medium was aspirated, the monolayers were washed twice with 5 ml cold PBS, and the cells were mock-infected or infected with vaccinia virus VC-2, vP872, or vP1033 at an moi of 5 in 0.5 ml D-MEM without additives. Virus was adsorbed for 1 hour at 37° C., then the inoculum was aspirated and fresh D-MEM containing 5% FBS+2mM L-glutamine+1% Penicillin-Streptomycin. Monolayers were harvested at 5 hpi by washing once in cold isotonic lysis buffer (35 mM Tris, pH 7.0; 146 mM NaCl; 11 mM glucose) followed by scraping cells into 5 ml isotonic lysis buffer followed by centrifugation for 10 minutes at 1,000 rpm. Supernatant removed and cell pellet lysed in 100 μl NP-40 lysis buffer (20 mM HEPES, pH 7.6; 120 mM KCl; 5 mM $MgCl_2$; 1 mM DTT; 10% glycerol; 0.5% NP-40). Five μl of the above lysate from uninfected or virus-infected cells was added to 5 μl lysate from IFN-treated uninfected cells in a 1.5 ml Eppendorf tube. Five μl P1 kinase assay buffer (60 mM HEPES, pH 7.5; 210 mM KCl; 25 mM MgOAc; 3 mM DTT; 2.5 mM ATP), 5 μl dsRNA (Pharmacia LKB Biotechnology, Piscataway, N.J.; 0, 0.1, 1, or 10 μg/ml) and 5 μl $^{32}$Pi (2mCi/ml, 3000Ci/mmol; dupont deNemours, Wilmington, Del.) were then added. Reactions were incubated 30 minutes at 30° C. Reactions were stopped by the addition of 25 μl 2x Laemmli sample buffer. Samples were boiled 3 minutes and fractionated on 12.5% SDS-PAGE. Gels were fixed, and an autoradiograph obtained.

A P1 kinase assay using lysate from uninfected or vaccinia virus-infected L929 cells was performed. The results demonstrate that vP872 and vP1033, the K3L-minus recombinants derived from VC-2 and WR, respectively, were able to inhibit phosphorylation of the P1 kinase to the same extent as wild-type VC-2. With uninfected cells, the P1 kinase was phosphorylated in the presence of 1 and 10 ug/ml poly(I)·poly(C). With all of the vaccinia viruses tested, VC-2, vP872, and vP1033, P1 kinase was not phosphorylated except in the presence of 10 ug/ml poly(I)·poly(C). It took ten times higher concentrations of poly(I)·poly(C) to activate the P1 kinase in cells infected with the vaccinia viruses. This corroborates observations made previously for the effect of vaccinia virus infection on the phosphorylation of P1 kinase (30). The inhibitory effect of P1 kinase phosphorylation is probably due to the action of a vaccinia virus encoded double-stranded RNA binding protein (31), which has characteristics consistent with the previously identified SKIF protein (30). That the phosphorylation of P1 kinase in vaccinia infected cells (wild-type or K3L-deletion mutants) was similar is consistent with the hypothesis that the presence of K3L probably acts mechanistically by preventing the phosphorylation of eIF2-α by P1 kinase.

EXAMPLE 7

Sensitivity of Fowlpox Virus and Canarypox Virus to chicken Interferon

Of the avipox viruses, only fowlpox virus has been tested for interferon sensitivity and was shown to be resistant to the antiviral effects of interferon in chick embryo fibroblasts treated with chicken interferon (32). To investigate the sensitivity of canarypox virus to interferon the following experiment was performed. Chicken embryo fibroblasts from 11 day old chicks (Select Laboratories, Gainesville, Ga.) were plated at $1.2 \times 10^7$ cells per 60 mm dish. Thirty minutes after plating, chicken interferon (Dr. Philip I. Marcus, University of Connecticut at Storrs; 20,000 units/ml) was added to the dishes at a final concentration of 0, 10, 100, or 1000 units/mi. After 24 hours, the medium was aspirated and the monolayers were infected with fowlpox virus or canarypox virus at an moi of 0.1 in 0.2 ml serum-free medium. The virus was adsorbed for 1 hour at 37° C. with rocking every 10 minutes. At the end of the adsorption period, the inoculum was aspirated and 2 ml fresh medium was added to the dishes. Virus was harvested at 72 hours post-infection by three cycles of freeze-thawing. Virus titrations were performed on CEF monolayers.

Figure 6:
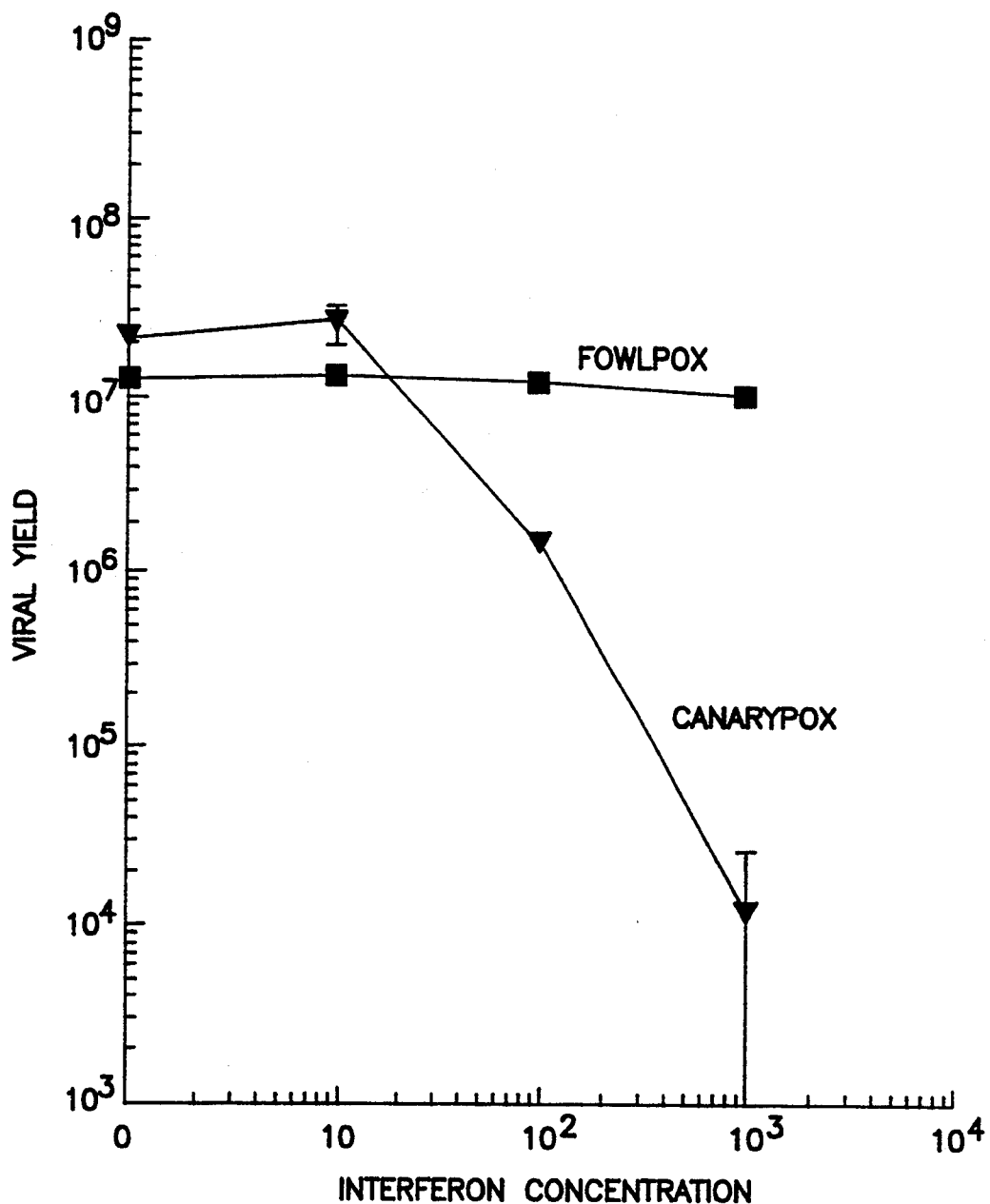
FIG. 6 is a plot of viral yields versus interferon concentration for fowlpox and canarypox viruses.

FIG. 6 shows the results of a yield reduction experiment. It can be seen that fowlpox virus was not inhibited by any of the concentrations of interferon tested in this experiment. Canarypox virus, on the other hand, was inhibited by interferon concentrations greater than 100 units/ml and at an interferon concentration of 1000 units/ml was approximately equal to residual input virus of $4.9 \times 10^3$. The demonstrated sensitivity of canarypox virus to interferon (FIG. 6) shows the ability to utilize interferon as an antiviral agent in the event of any post-vaccination complication induced by a canarypox based recombinant virus vaccine.

This example illustrates that a poxvirus having an open reading frame for interferon resistance disrupted or deleted therefrom is useful as a vaccine. Example 22 of U.S. application Ser. No. 07/537,890 filed Jun. 14, 1990 shows the utility of a recombinant canarypox virus containing exogenous DNA coding for rabies. As shown herein, canarypox virus naturally fails to have resistance to the antiviral effects of interferon. Thus, a recombinant poxvirus containing exogenous DNA coding for an antigen and having the open reading frame for interferon resistance deleted therefrom functions as the recombinant canarypox virus of Example 22 of Ser. No. 07/537,890, filed Jun. 14, 1990; namely, that it will express the antigen (and thus elicit an immune response in the host), yet be able to be "turned off" by the administration of exogenous interferon. Furthermore, the techniques of the earlier Paoletti applications (mentioned above and incorporated by reference) can be used to prepare recombinant poxviruses containing exogenous DNA, and the techniques disclosed herein are used on such recombinant poxviruses to delete resistance to interferon, thereby yielding the especially useful viruses of this invention (containing exogenous DNA and having interferon resistance deleted). Likewise, the skilled artisan can employ the techniques herein and then the techniques of the earlier Paoletti applications to produce recombinant poxviruses containing exogenous DNA and having interferon resistance deleted therefrom.

REFERENCES

1. Hovanessian, A.G., J. Ifn. Res. 9, 641–647 (1989). 1.
2. Joklik, W.K., In Interferons in Virology, eds. Fields, B.N., and Knipe, D.M., Raven Press, Ltd., New York, 383–410 (1990).
3. Paez, E., and Esteban, M., Virology 134, 12–28 (1984).
4. Rice, A.P. and Kerr, I.M., J. Virol. 50, 209–228 (1984).
5. Whitaker-Dowling, P-, and Youngner, J.S., Virology 131, 128–136 (1983).
6. Whitaker-Dowling, P., and Youngner, J.S., Virology 152, 50–57 (1986) .
7. Goebel, S.J., Johnson, G.P., Perkus, M.E., Davis, S.W., Winslow, J.P., and Paoletti, E., Virology 179, 247–266, 517–563 (1990).
8. Ernst, H., Duncan, R.F., and Hershey, J.W.B., J. Biol. Chem. 262, 1206–1212 (1987).
9. Pathak, V., Schindler, D., and Hershey, J.W.B., Mol. Cell. Biol. 8, 993–995 (1988).
10. Kaufman, R.J., Davies, M.V., Pathak, V.K., and Hershey, J.W.B., Mol. Cell. Biol. 9, 946–958 (1989).
11. Davies, M.V., Furtado, M., Hershey, J.W.B., Thimmappaya, B., and Kaufman, R.J., Proc. Natl. Acad. Sci. 86, 9163–9167 (1989).
12. Dratewka-Kos, E., Kiss, I., Lucas-Lenard, J., Mehta, H.B., Woodley, C.L., and Wahba, A.J., Biochem. 23, 6184–6190 (1984).
13. Boursnell, M.E.G., Foulds, I.J., Campbell, J.I., and Binns, M.M., J. gen. Virol. 69, 2995–3003 (1988).
14. Tartaglia, J., Pincus, S., and Paoletti, E., Crit. Rev. Immunol. 10, 13–30 (1990).

15. Lipman, D.J., and Pearson, W.R., Science 227, 1435–1441 (1985).
16. Pickup, D.J., Ink, B.S., Hu, W., Ray, C.A., and Joklik, W.K., Proc. Natl. Acad. Sci. 83, 7698–7702 (1986).
17. Piccini, A., Perkus, M.E., and Paoletti, E., In Meth. Enzymol., eds. Wu, R., and Grossman, L., Academic Press, New York 153, 545–563 (1987).
18. Boyle, D.B., and Coupar, B.E.H., Gene 65, 123–128 (1988).
19. Falkner, F., and Moss, B., J. Virol. 62, 1849–1854 (1988).
20. Clewell, D.B., J. Bacteriol. 110, 667–676 (1972).
21. Clewell, D.B. and Helinski, D.R., Proc. Natl. Acad. Sci. USA 62, 1159–1166 (1969).
22. Maniatis, T., Fritsch, E.F., and Sambrook, J., Molecular Cloning, Cold Spring Harbor Laboratory, NY 545 pages (1982).
23. Taylor, J., Weinberg, R., Kawaoka, L., Webster, R.G., and Paoletti, E., Vaccine 6, 504–506 (1988).
24. Taylor, J-, Weinberg, R., Lanquet, B., Desmettre, P., and Paoletti, E., Vaccine 6, 497–504 (1988).
25. Yuen, L. and Moss, B., Proc. Natl. Acad. Sci. USA 84, 6417–6421 (1987).
26. Engelke, D.R., Hoener, P.A., and Collins, F.S., Proc. Natl. Acad. Sci. USA 85, 544–548 (1988).
27. Dreyfuss, G., Adam, S.A., and Choi, Y.D., Mol. Cell. Biol. 4, 415 (1984).
28. Kieny, M.P., Lathe, R., Drillien, R., Spehner, D., Skory, S., Schmitt, D., Wiktor, T., Koprowski, H., and Lecocq, J. P., Nature (London) 312, 163–166 (1984).
29. Coccia, E.M., Romeo, G., Nissim, A., Marziali, G., Albertini, R., Affabris, E., Battistini, A., Fiorucci, G., Orsatti, R., Rossi, G.B., and Chebath, J-, Virology 179, 228–233 (1990).
30. Whitaker-Dowling, P-, and Youngner, J.S., Virology 137, 171–181 (1984).
31. Watson, J.C., Hwai-Wen, C., and Jacobs, B.L., Virology 185, 206–216 (1991).
32. Asch, B.B. and Gifford, G.E., Proc. Soc. Exp. Med. Biol. 135, 419–422 (1970).

---

What is claimed is:

1. A recombinant poxvirus modified to have an open reading frame conferring interferon disrupted or deleted therefrom, said open reading frame having homology to eIF-2alpha or K3L open reading frame of vaccinia.

2. A recombinant poxvirus as in claim 1 wherein the poxvirus is a vaccinia virus.

3. A recombinant vaccinia virus as in claim 2 wherein the open reading frame is K3L open reading frame.

4. A recombinant poxvirus as in claim 1 wherein the open reading frame is deleted.

5. A recombinant poxvirus as in claim 4 wherein said open reading frame has homology with eIF-2alpha, 6. A recombinant poxvirus as in claim 4 wherein the poxvirus is a vaccinia virus.

7. A recombinant vaccinia virus as in claim 6 wherein the open reading frame is K3L open reading frame.

8. A recombinant poxvirus synthetically modified to disrupt gene expression of a gene conferring interferon resistance; said gene having homology to eIF-2alpha or K3L open reading frame of vaccinia.

9. A recombinant poxvirus as in claim 8 wherein the poxvirus is a vaccinia virus.

10. A recombinant vaccinia virus as in claim 9 wherein to disrupt gene expression of a gene conferring interferon resistance, a K3L open reading frame is disrupted.

11. A vaccine comprising a carrier and a recombinant poxvirus as claimed in claim 1.

12. A vaccine for inducing an antigenic comprising a carrier and a recombinant poxvirus as claimed in claim 4.

13. A vaccine comprising a carrier and a recombinant poxvirus as claimed in claim 8.

14. An immunological composition for inducing an immunological response in a host animal inoculated with said composition, said composition comprising a carrier and a recombinant poxvirus as claimed in claim 1.

15. An immunological composition for inducing an immunological response in a host animal inoculated with said composition, said composition comprising a carrier and a recombinant poxvirus as claimed in claim 4.

16. An immunological composition for inducing an immunological response in a host animal inoculated with said composition, said composition comprising a carrier and a recombinant poxvirus as claimed in claim 8.

* * * * *

UNITED STATES PATENT AND TRADEMARK OFFICE
CERTIFICATE OF CORRECTION

PATENT NO. : 5,378,457

DATED : January 3, 1995

INVENTOR(S) : Enzo Paoletti et al.

It is certified that error appears in the above-identified patent and that said Letters Patent is hereby corrected as shown below:

Claim 1, line 1, (column 25, line 18), after "poxvirus" insert --synthetically--;

line 2, (column 25, line 19), after "conferring" insert --resistance to--.

Signed and Sealed this

Fourteenth Day of March, 1995

Attest:

BRUCE LEHMAN

Attesting Officer

Commissioner of Patents and Trademarks

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
    (A) LENGTH: 90 amino acids
    (B) TYPE: amino acid
    (C) STRANDEDNESS: single
    (D) TOPOLOGY: linear (xi) SEQUENCE DESCRIPTION: SEQ ID NO:1:

```
Met Leu Ala Phe Cys Tyr Ser Leu Pro Asn Ala Gly Asp Val Ile Lys
 1               5                  10                  15

Gly Arg Val Tyr Glu Xaa Lys Asp Tyr Ala Leu Tyr Ile Tyr Leu Phe
                20                  25                  30

Asp Tyr Pro His Ser Glu Ala Xaa Ile Leu Ala Glu Ser Val Lys Met
             35                  40                  45

His Met Asp Arg Tyr Val Glu Tyr Arg Asp Lys Leu Val Gly Lys Thr
     50                  55                  60

Val Lys Val Lys Val Ile Arg Val Asp Tyr Thr Lys Gly Tyr Ile Asp
 65                  70                  75                  80

Val Asn Tyr Lys Arg Met Cys Arg His Gln
                 85                  90
```

(2) INFORMATION FOR SEQ ID NO:2:

(i) SEQUENCE CHARACTERISTICS:
    (A) LENGTH: 316 amino acids
    (B) TYPE: amino acid
    (C) STRANDEDNESS: single
    (D) TOPOLOGY: linear (xi) SEQUENCE DESCRIPTION: SEQ ID NO:2:

```
Met Pro Gly Leu Ser Cys Arg Phe Tyr Gln His Lys Phe Pro Glu Val
 1               5                  10                  15

Glu Asp Val Val Met Val Asn Val Arg Ser Ile Ala Glu Met Gly Ala
                20                  25                  30

Tyr Val Ser Leu Leu Glu Tyr Asn Asn Ile Glu Gly Met Ile Leu Leu
             35                  40                  45
```

```
    Ser Glu Leu Ser Arg Arg Arg Ile Arg Ser Ile Asn Xaa Lys Leu Ile
        50                  55                  60

Arg Ile Gly Arg Asn Glu Cys Val Val Val Ile Arg Val Asp Lys Glu
    65                  70                  75                  80

Lys Gly Tyr Ile Asp Leu Ser Lys Arg Arg Val Ser Pro Glu Glu Ala
                    85                  90                  95

Ile Lys Cys Glu Asp Lys Phe Thr Lys Ser Lys Thr Val Tyr Ser Ile
                    100                 105                 110

Leu Arg His Val Ala Glu Val Leu Glu Tyr Thr Lys Asp Glu Gln Leu
            115                 120                 125

Glu Ser Leu Phe Gln Arg Thr Ala Trp Val Phe Asp Asp Lys Tyr Lys
        130                 135                 140

Arg Pro Gly Tyr Gly Ala Tyr Asp Ala Phe Lys His Ala Val Ser Asp
    145                 150                 155                 160

Pro Ser Ile Leu Asp Ser Leu Asp Leu Asn Glu Asp Glu Arg Glu Val
                    165                 170                 175

Leu Ile Asn Asn Ile Asn Arg Arg Leu Thr Pro Gln Ala Val Lys Ile
                180                 185                 190

Arg Ala Asp Ile Glu Val Ala Cys Tyr Gly Tyr Glu Gly Ile Asp Ala
            195                 200                 205

Val Lys Glu Ala Leu Arg Ala Gly Leu Asn Cys Ser Thr Glu Thr Met
    210                 215                 220

Pro Ile Lys Ile Asn Leu Ile Ala Pro Pro Arg Tyr Val Met Thr Thr
    225                 230                 235                 240

Thr Thr Leu Glu Arg Thr Glu Gly Leu Ser Val Leu Asn Gln Ala Met
                    245                 250                 255

Ala Val Ile Lys Glu Lys Ile Glu Glu Lys Arg Gly Val Phe Asn Val
                260                 265                 270

Gln Met Glu Pro Lys Val Val Thr Asp Thr Asp Glu Thr Glu Leu Ala
            275                 280                 285

Arg Gln Leu Glu Arg Leu Glu Arg Glu Asn Ala Glu Val Asp Gly Asp
        290                 295                 300

Asp Asp Ala Glu Glu Met Glu Ala Lys Ala Glu Asp
    305                 310                 315
```

( 2 ) INFORMATION FOR SEQ ID NO:3:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:3:

ATCATCAAGC TTGTTAACGG GCTCGTAAAT TGG    33

( 2 ) INFORMATION FOR SEQ ID NO:4:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:4:

ATCGATATTT TTATGCGTGA TTGG    24

( 2 ) INFORMATION FOR SEQ ID NO:5:

( i ) SEQUENCE CHARACTERISTICS:
      ( A ) LENGTH: 29 base pairs (B) TYPE: nucleic acid
    (C) STRANDEDNESS: single
    (D) TOPOLOGY: linear (xi) SEQUENCE DESCRIPTION: SEQ ID NO:5:

ATCATCAAGC TTTAATTTTT ATACCGAAC                                            29

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

ATCATCCTCG AGGCAGGCAA TAGCGACATA AAC                                       33

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:7:

ATCATCAAGC TTTTATTGAT GTCTACACAT CC                                        32

(2) INFORMATION FOR SEQ ID NO:8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:8:

GGGCTCAAGC TTGCGGCCGC TCATTAGACA AGCGAATGAG GGAC                           44

(2) INFORMATION FOR SEQ ID NO:9:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:9:

AGATCTCCCG GGCTCGAGTA ATTAATTAAT TTTATTACA CCAGAAAAGA CGGCTTGAGA           60
TC                                                                        62

(2) INFORMATION FOR SEQ ID NO:10:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:10:

TAATTACTCG AGCCCGGGAG ATCTAATTTA ATTAATTTA TATAACTCAT TTTTTGAATA           60
TACT                                                                      64

(2) INFORMATION FOR SEQ ID NO:11:

(i) SEQUENCE CHARACTERISTICS:
        (A) LENGTH: 45 base pairs ( B ) TYPE: nucleic acid
        ( C ) STRANDEDNESS: single
        ( D ) TOPOLOGY: linear ( x i ) SEQUENCE DESCRIPTION: SEQ ID NO:11:

TATCTCGAAT TCCCGCGGCT TTAAATGGAC GGAACTCTTT TCCCC   45

( 2 ) INFORMATION FOR SEQ ID NO:12:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CCTTATTTTT ATGTTCGGTA TAAAAATTAA AGCTTCTTGT TAACGGGCTC GTAAATTGG   59

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATCATCTCTA GAGAATTAAG AAGATCCGC   29

( 2 ) INFORMATION FOR SEQ ID NO:14:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCAATTTACG AGCCCGTTAA CAAGAAGCTT TAATTTTTAT ACCGAACATA AAAATAAGG   59

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GCGTGTTTTA GTGATATCAA ACGG   24

( 2 ) INFORMATION FOR SEQ ID NO:16:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CTGAAATTAT TCATTATCG CGATATCCGT TAAGTTTGTA TCGTAATGGT TCCTCAGGCT   60

CTCCTGTTTG T   71

( 2 ) INFORMATION FOR SEQ ID NO:17:

( i ) SEQUENCE CHARACTERISTICS:
        ( A ) LENGTH: 48 base pairs
        ( B ) TYPE: nucleic acid
        ( C ) STRANDEDNESS: single (D) TOPOLOGY: linear (xi) SEQUENCE DESCRIPTION: SEQ ID NO:17:

CATTACGATA CAAACTTAAC GGATATCGCG ATAATGAAAT AATTTCAG  48

(2) INFORMATION FOR SEQ ID NO:18:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:18:

ACCCCTTCTG GTTTTTCCGT TGTGTTTTGG GAAATTCCCT ATTTACACGA TCCCAGACAA  60

GCTTAGATCT CAG  73

(2) INFORMATION FOR SEQ ID NO:19:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:19:

CTGAGATCTA AGCTTGTCTG GATCGTGTA AATAGGGAAT TTCCCAAAAC A  51

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:20:

CAACGGAAAA ACCAGAAGGG GTACAAACAG GAGAGCCTGA GGAAC  45

(2) INFORMATION FOR SEQ ID NO:21:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:21:

GGATCCCCGG G  11

(2) INFORMATION FOR SEQ ID NO:22:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:22:

ACTCTCAAAA GCTTCCCGGG AATTCTAGCT AGCTAGTTTT TATAAA  46

(2) INFORMATION FOR SEQ ID NO:23:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (x i) SEQUENCE DESCRIPTION: SEQ ID NO:23:

GATCTTTATA AAAACTAGCT AGCTAGAATT CCCGGGAAGC TTTTGAGAGT        50

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (x i) SEQUENCE DESCRIPTION: SEQ ID NO:24:

GCTTCCCGGG AATTCTAGCT AGCTAGTTT        29